United States Patent [19]

Sakai et al.

[11] Patent Number: 4,672,078

[45] Date of Patent: Jun. 9, 1987

[54] UREA STABILIZED WITH A LACTONE IN VARIOUS PHARMACEUTICAL AND COSMETIC PREPARATIONS

[75] Inventors: Kirk Sakai, Coral Springs; Timothy W. Quick, Pembroke Pines, both of Fla.

[73] Assignee: Schering-Plough Corporation, Kenilworth, N.J.

[21] Appl. No.: 752,263

[22] Filed: Jul. 3, 1985

[51] Int. Cl.$^4$ ...................... A61K 31/17; A61K 47/00
[52] U.S. Cl. .................................... 514/588; 514/788; 514/970
[58] Field of Search ......................... 514/588, 788, 970

[56] References Cited

U.S. PATENT DOCUMENTS 3,666,863 5/1972 Swanbeck .......................... 424/316
4,291,062 9/1981 Leigh et al. ......................... 424/322

FOREIGN PATENT DOCUMENTS 1404583 9/1975 United Kingdom ................ 514/588

Primary Examiner—Frederick E. Waddell
Attorney, Agent, or Firm—John J. Maitner; Stephen I. Miller; James R. Nelson

[57] ABSTRACT

A pharmaceutical preparation containing 1 to 50% urea and 0.05 to 30% of a lactone is disclosed. A preferred lactone is gamma-butyrolactone which is preferably present in an amount of about 0.05 to 0.1 part by weight per 1 part by weight of urea. The lactone stabilizes the urea with respect to various parameters including changes in pH. The pharmaceutical preparation may be any preparation with stabilized urea such as a skin lotion or cream used to moisturize skin, or a post surgical preparation because urea aids in debridement, dissolves coagulum and promotes epithelialization. Alternatively the preparation may be an injectable solution used in the treatment for mobilization of edema fluid, as urea is used for an osmotic diuretic.

14 Claims, 15 Drawing Figures

Fig.1
30% UREA AQUEOUS SOLUTION WITH VARIOUS CONCENTRATIONS OF BUTYROLACTONE AT 45°C.

Fig.2
50% UREA AQUEOUS SOLUTION WITH/WITHOUT 5% BUTYROLACTONE AT VARIOUS TEMPERATURES

Fig. 3

30% UREA AQUEOUS SOLUTION WITH/WITHOUT 3% BUTYROLACTONE AT VARIOUS TEMPERATURES

□ ROOM TEMP. X-45°C ◆ 37°C

Fig. 4

10% UREA AQUEOUS SOLUTION WITH/WITHOUT 1% BUTYROLACTONE AT VARIOUS TEMPERATURES

□ ROOM TEMP. X-37°C ◆ 45°C

Fig. 5

THE CHANGE IN PH OVER TIME OF VARIOUS CONCENTRATIONS OF UREA AQUEOUS SOLUTIONS STARTING WITHOUT BUTYROLACTONE AND THEREAFTER ADDING BUTYROLACTONE.

Fig. 6

THE CHANGE OF PH OVER TIME OF A 10% UREA CREAM WITHOUT BUTYROLACTONE AT VARIOUS TEMPERATURES

Fig. 7

THE CHANGE OF PH OVER TIME OF A 10% UREA CREAM CONTAINING 1% BUTYROLACTONE AT VARIOUS TEMPERATURES

Fig. 8

THE CHANGE IN VISCOSITY OVER TIME OF A 10% UREA CREAM WITH AND WITHOUT 1% BUTYROLACTONE.

Fig. 9

THE CHANGE IN PH OVER TIME OF A 25% UREA LOTION WITHOUT BUTYROLACTONE AT VARIOUS TEMPERATURES

Fig. 10

THE CHANGE IN PH OVER TIME OF A 25% UREA LOTION WITH 2% BUTYROLACTONE AT VARIOUS TEMPERATURES

Fig.11

THE CHANGE IN VISCOSITY OVER TIME OF A 25% UREA LOTION WITH AND WITHOUT 2% BUTYROLACTONE

Fig.12

THE CHANGE IN PH TIME OF A 0.1% TRIAMCINOLONE AND 10% UREA PREPARATION AT VARIOUS TEMPERATURES

Fig.13
THE CHANGE OF PH OVER TIME OF A 0.1% TRIAMCINOLONE AND 10% UREA PREPARATION WITH 1% BUTYROLACTONE AT VARIOUS TEMPERATURES.

Fig.14
THE CHANGE IN PH OVER TIME OF A 0.1% BETAMETHASONE AND 10% UREA PREPARATION AT VARIOUS TEMPERATURES.

Fig.15
THE CHANGE IN PH OVER TIME OF A 0.1% BETAMETHASONE AND 10% UREA PREPARATION WITH 1% BUTYROLACTONE AT VARIOUS TEMPERATURES

UREA STABILIZED WITH A LACTONE IN VARIOUS PHARMACEUTICAL AND COSMETIC PREPARATIONS

BACKGROUND OF THE INVENTION

This invention relates to stabilized urea (carbamide) compositions in various pharmaceutical and cosmetic preparations, and more particularly to such compositions stabilized by the addition of a lactone, preferably gamma-butyrolactone.

The value of urea in pharmaceutical and cosmetic preparations has been recognized since the early days of folk medicine. It is known that 10–30 percent urea is mildly keratolytic and increases water uptake in the stratum corneum. This gives it a high water-binding capacity which leads to the use of urea as a skin moisturizer, or as a transdermal drug penetration enhancer. Urea also aids in debridement, dissolves the coagulum and promotes epithelialization when used in a concentration of approximately 10–15 percent. At higher concentrations, e.g. above 40 percent, urea is proteolytic and therefore, is used for the treatment of nail destruction and dissolution. Furthermore for treatment for mobilization of edema fluid, urea is used as an osmotic diuretic. Nevertheless, urea has been found to be unsuitable in many pharmaceutical and cosmetic preparations because it tends to be unstable, with the urea hydrolyzing into ammonium cyanate. Although the degree of urea degradation is generally small, the untoward effects, such as ammoniacal odor and pH shift to alkali, can be very sifignificant. The ammoniacal odor and increased pH are known to result from ammonia production, which occurs in the following manner when urea is present:

$$(NH_2)_2CO = NH_4^+ + CNO^- \qquad (A)$$

$$NH_4^+ + H_2O = NH_3 + H_3O^+ \qquad (B)$$

To cope with the adverse effects caused by urea degradation, numerous attempts were made in the past to stabilize the urea preparation through the use of buffers or acids to neutralize the ammonia produced by urea breakdown. These methods have not been very satisfactory, however, because the acidification tends to accelerate the process of decomposition. Another problem in the use of acidic preparations in pharmaceutical and cosmetic products has been the burning or stinging sensation that occurs when topical preparations containing urea are applied to the skin.

SUMMARY OF THE INVENTION

The present inventors have now found that urea can be maintained in a substantially stable state by the addition of a small amount of a lactone, which term is intended to include thiolactones as well.

Good results have been obtained by the use of lactones of the general formula:

(1)

wherein X is oxygen or sulfur, R is hydrogen or lower alkyl, and Z represents an optionally substituted atomic group necessary to form a carbocyclic ring.

The following lactones, which all come within the above general formula, are all well known and commercially available. They were all found to be useful for preventing or reducing urea deterioration and for reducing ammoniacal odor. A structural representation of each lactone is shown below its name:

gamma-butyrolactone,         beta-butyrolactone, gamma-thiobutyrolactone,     2-acetyl-gamma-butyrolactone, gamma-valerolactone,         delta-valerolactone, gamma-octanoiclactone, and   epsilon-caprolactone.

Based on our findings that gamma-butyrolactone possesses better urea stabilizing capability, better solubility in both hydrophilic and lipophilic solvents, and better odor than other lactones, it is preferred over other lactones in pharmaceutical and cosmetic preparations. It is also a non-toxic, non-corrosive, chemically stable liquid which has outstanding commercial utility in various fields.

It is therefore an object of the present invention to provide a a urea-containing composition wherein the urea is stabilized from denaturalization.

Another object of this invention is to provide a method for stabilizing the urea in urea-containing compositions.

A further object of this invention is to provide a process whereby compositions containing degraded urea may be stabilized against further degradation and ammonia formation, and restored to normal pH.

Yet another object of this invention is to provide topical pharmaceutical and cosmetic preparations containing stabilized urea.

These and other objects of the invention will become apparent to those skilled in the art upon reading the present disclosure.

BRIEF DESCRIPTION OF THE DRAWINGS

In the following drawings and throughout the discussion thereof, the terms butyrolactone and BLO are intended to mean gamma-butyrolactone.

DETAILED DESCRIPTION OF THE INVENTION

The aforementioned objects of this present invention are achieved by the incorporation or addition of a lactone to a water-based pharmaceutical preparation containing urea. The amount of urea in such preparations may be as little as about 1 percent by weight or as high as about 50% by weight. Below 1 percent, the urea concentration would generally be too low to be pharmaceutically useful, while the upper limit of about 50% is based on the solubility limit of urea in water.

The amount of lactone added to the preparation should be in the range of about 0.05 to about 30 percent by weight. Below about 0.05 percent, the lactone is generally ineffective. Amounts of lactone in excess of about 30 percent by weight have been found to be unnecessary and wasteful. Preferably no more than about 10 percent, and more preferably, no more than about 2.5 percent by weight lactone is used. Furthermore, the amount of lactone used is preferably also based on the amount of urea present. Good results were obtained when the amount of lactone used was about 5 to about 10 percent by weight of the weight of urea in the preparation, with lactone at about 10 percent by weight of urea providing particularly good results.

A variety of lactones, including thiolactones, have been found to be useful in the present invention. A preferred general formula for the lactones of the present invention is presented above as Formula (1).

As discussed previously, the following lactones, all within the above general formula, were found to be effective in stabilizing urea in accordance with the present invention:

| gamma-butyrolactone, | beta-butyrolactone, |
| gamma-thiobutyrolactone, | 2-acetyl-gamma-butyrolactone, |
| gamma-valerolactone, | delta-valerolactone, |
| gamma-octanoiclactone, and | epsilon-caprolactone. |

Of these, gamma-butyrolactone, hereinafter referred to simply as butyrolactone or BLO, was found to be the most suitable for use in topical pharmaceutical and cosmetic preparations for the reasons discussed previously.

The following examples of preferred embodiments of the present invention were all prepared using gamma-butyrolactone. In all cases, the indicated weight percents are proportionally based on the weight in grams of material added to a 100 ml container which is then filled with water to make the composition. This type of percentage will be referred to as w/v or weight per volume. It is to be understood that in the following examples, unless otherwise stated, all concentrations expressed as percent refer to percent w/v.

EXAMPLE 1

Various concentrations of butyrolactone (BLO) were added to 30 percent urea aqueous solutions in order to examine the effects on pH and active urea concentrations. Solutions were made containing 30 percent urea with 0, 1.5, 3, 10, and 30 percent BLO. The solutions were allowed to stand for 90 days at 45° C. with periodic measurement of pH and percent available urea.

Figure 1:
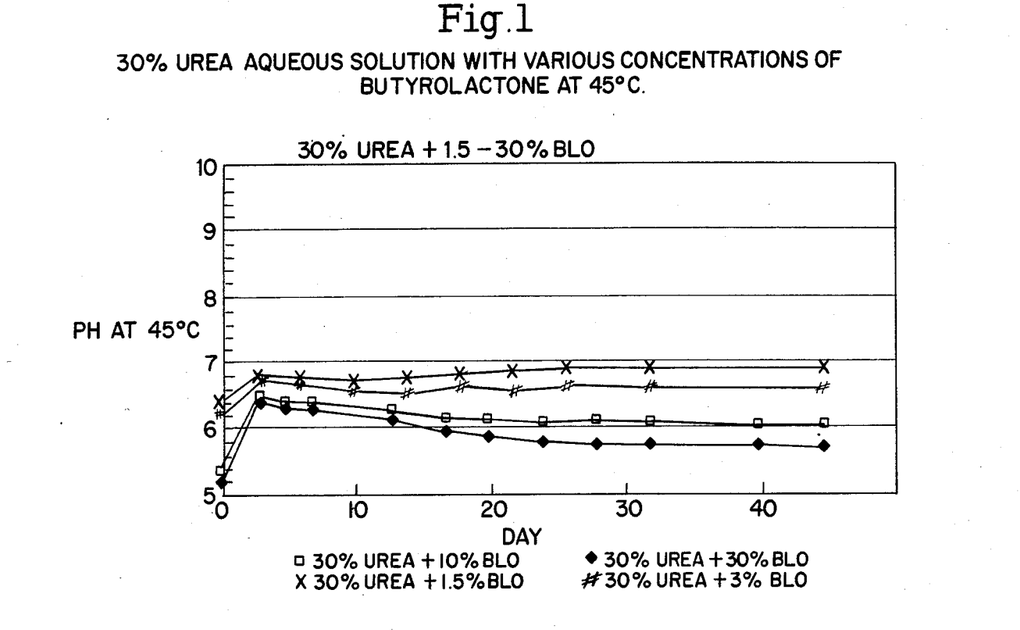
FIG. 1 is a graph wherein the change in pH with respect to time has been plotted for a 30 percent urea aqueous solution containing various concentrations of butyrolactone at 45° C.

FIG. 1 is a graphical representation of the pH of the various BLO-containing solutions over the initial 45-day period. The results show that all these BLO-containing solutions remained at a pH of between 5.5 and 7 throughout this period. This would generally be considered a suitable pH for pharmaceutical preparations, praticularly topical dermatological creams and lotions. On the other hand, the pH of the 30 percent urea preparation without BLO rose rapidly. After 10 days, the pH had reached 8.6, by 20 days the pH was over 8.9 and after 45 days, the pH was at 9.3. The data for the control test without BLO is presented graphically as the 45° C. test in FIG. 3, discussed below.

Another indication of the denaturalization of the urea composition without BLO was the distinct ammoniacal odor which it had after 45 days. In comparison, none of the BLO-containing preparations had any noticeable ammoniacal odor, further evidence of the urea stabilization provided by the present invention.

A further factor to be considered in regard to this invention is whether or not the addition of a lactone to a composition significantly affects the amount of available urea in that composition. For the compositions of EXAMPLE 1, the amount of available urea was determined at day 45 and day 90. The results, set forth in TABLE 1 below, show that the addition of the BLO to the urea compositions had only a nominal effect on the amount of available urea. The amount of available urea in the worst case (30% BLO) was still more than 98% of what it would have been if no BLO had been added.

TABLE 1

| Composition | UREA CONCENTRATION (g/100 ml) AT 45° C. | | | | |
|---|---|---|---|---|---|
| | Initial | Day 45 | (% change) | Day 90 | (% change) |
| 30% urea | 30.58 | 30.19 | (−1.28%) | 30.15 | (−1.41%) |
| 30% urea + 1.5% BLO | 30.77 | 30.31 | (−1.49%) | 30.29 | (−1.62%) |
| 30% urea + 3% BLO | 31.01 | 30.44 | (−1.84%) | 30.31 | (−2.26%) |
| 30% urea + 10% BLO | 30.93 | 30.23 | (−2.26%) | 30.12 | (−2.62%) |
| 30% urea + 30% BLO | 29.91 | 29.14 | (−2.57%) | 29.02 | (−2.98%) |

(Data are based on the average of 3 experiments)

Higher amounts of BLO than those set forth above, under certain circumstances, may be used, but would normally be considered unnecessary. The gamma-butyrolactone may be added to the urea preparation as an aqueous solution, but other forms of gamma-butyrolactone are also suitable and may be used.

In addition to the above-described stabilizing effect of gamma-butyrolactone, other beneficial effects have been observed. Firstly, gamma-butyrolactone is neither a human skin irritant nor a skin sensitizer (Patty, F. A. ed., *Industrial Hygiene and Toxicology*, Vol. 2, New York, Interscience, pp 1824–1825, (1963)), and forms an injectable solution with sedative, hypnotic, and anesthetic effects (U.S. Pat. No. 3,051,619 Aug. 28, 1962 by H. M. Laborit). In addition, anticancer activity in mice has been reported (Tomita, M et al, *Z. Physiol. Chem.* 342: 177–82 (1965), and *Registering of Toxic Effects of Chemical Substances*, Vol. 1, NIOSH, p 834 (1980)). Secondly, gamma-butyrolactone is miscible in water in all proportions. Finally, it has been found that gamma-butyrolactone does not have adverse effects on the keratolytic, anticoagulative, epithelializational and osmotic diuretic activites of urea, that is, the mixture of gamma-butyrolactone and urea is pharmacologically as active as urea alone.

EXAMPLE 2

The following example illustrates the stabilizing effects of gamma-butyrolactone in various representative urea compositions.

Figure 2:
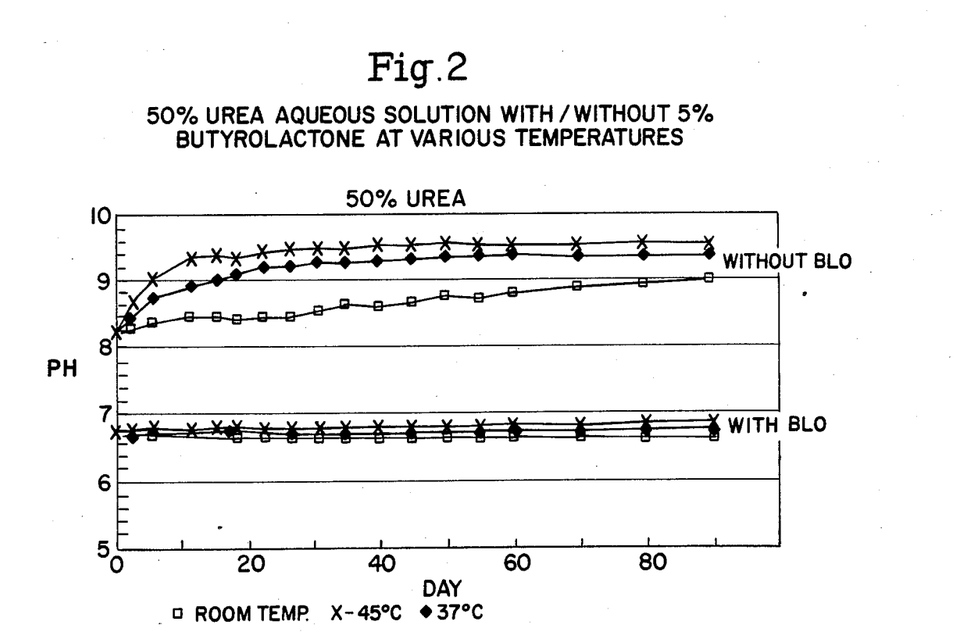
FIG. 2 is a graph showing the change in pH over time of a 50 percent urea aqueous solution with and without a 5 percent concentration of butyrolactone at various temperatures.
Figure 3:
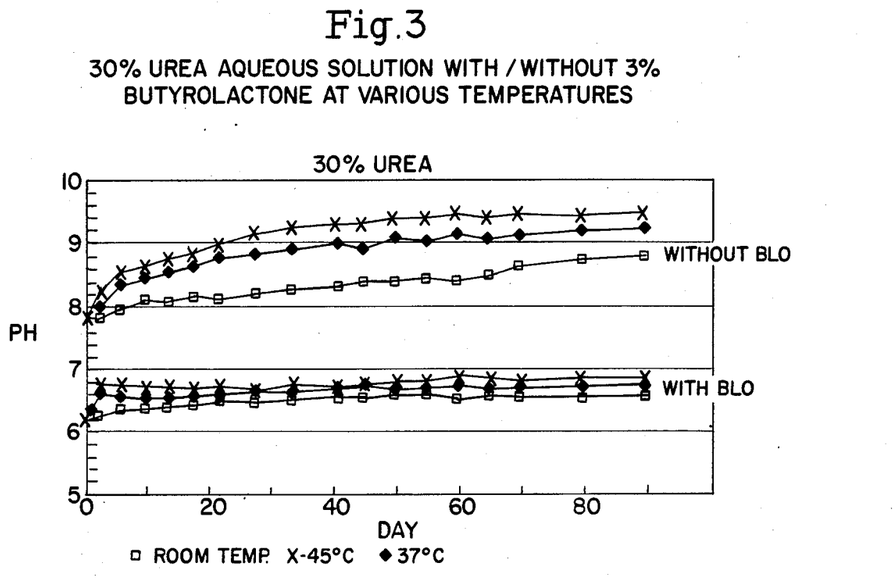
FIG. 3 is a graph showing the change in pH over time of a 30 percent urea aqueous solution with and without butyrolactone at various temperatures.
Figure 4:
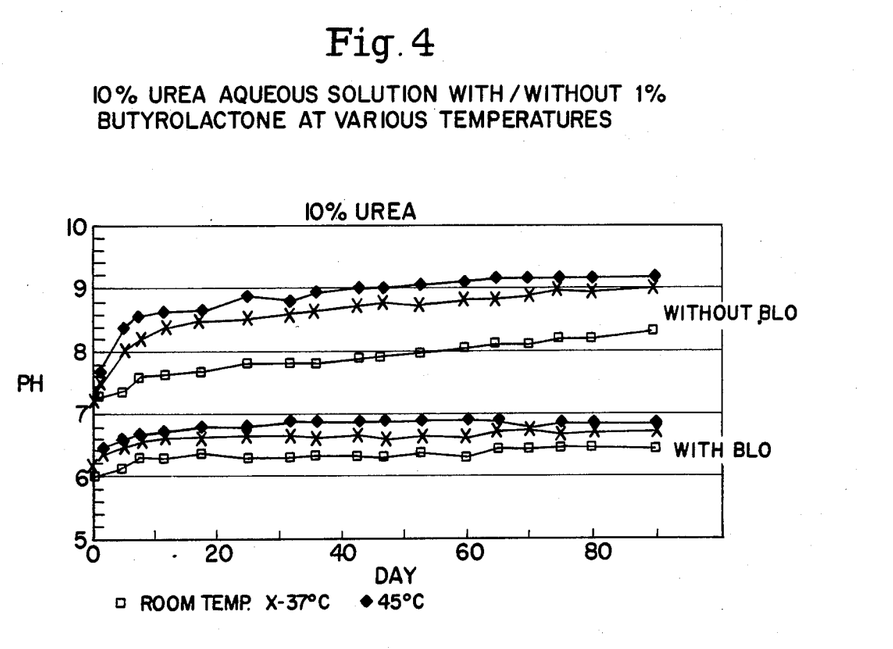
FIG. 4 is a graph showing the change in pH over time of a 10 percent urea aqueous solution with and without butyrolactone at various temperatures.

In oder to make 50, 30, and 10 w/v percent urea aqueous solutions, urea (USP grade) was dissolved in purified water (USP grade) at room temperature. Simultaneously, urea aqueous solutions which contain 0.1 part by weight of gamma-butyrolactone (BLO) per 1 part by weight urea were prepared (i.e. 5.0, 3.0, and 1.0 w/v percent BLO respectively). Separate samples of these urea solutions were maintained at room temperature (18°–27° C.) and under accelerated storage conditions at temperatures of 37° C. and 45° C. for up to 90 days. The pH's of these solutions were measured periodically, and the results are shown in FIGS. 2, 3, and 4.

The data for the 50% urea aqueous solution (FIG. 2) indicate that without butyrolactone the rate change of pH is dependent on the temperature. For example, samples maintained at 45° C. reach to the equilibrium state 2 to 3 times faster than the samples maintained at 37° C., and substantially faster than that of room temperature samples. However, the pH's of all samples which contained butyrolactone were not significantly temperature or time dependent. Similar results were obtained for the 30 and 10 percent urea tests as presented in FIGS. 3 and 4.

Over a 90 day study period, all urea aqueous solutions at 45° C. reached equilibrium states with pH's in the range of 9.1 to 9.6. Even the room temperature test solutions all reached equilibrium pH's of over 8. However, with butyrolactone the pH's of all urea aqueous solutions remained in the range of 6.3 to 6.9, even under the high temperature accelerated storage conditions.

The solutions were also analyzed to determine the amount of the active urea present initially (actually at 1 day), and at 45 days and 90 days (Table 2). Although slight increases of urea degradation were observed in the urea aqueous solutions containing butyrolactone, the differences between the groups with butyrolactone and without butyrolactone were extremely small.

TABLE 2

| | | CONCENTRATION OF UREA (g/100 ml) | | | | |
|---|---|---|---|---|---|---|
| | | Initial (1 Day) | 45 Day | (% change) | 90 day | (% change) |
| 10% urea | RT | 10.59 | 10.55 | (−0.38) | 10.51 | (−0.76) |
| | 37 C | 11.01 | 10.91 | (−0.91) | 10.87 | (−1.27) |
| | 45 C | 10.88 | 10.76 | (−1.10) | 10.72 | (−1.47) |
| 10% urea + 1% BLO | RT | 10.37 | 10.31 | (−0.58) | 10.27 | (−0.96) |
| | 37 C | 10.04 | 9.95 | (−0.90) | 9.88 | (−1.59) |
| | 45 C | 10.57 | 10.42 | (−1.42) | 10.37 | (−1.89) |
| 30% urea | RT | 30.69 | 30.53 | (−0.52) | 30.48 | (−0.68) |
| | 37 C | 31.04 | 30.85 | (−0.61) | 30.72 | (−1.03) |
| | 45 C | 31.11 | 30.69 | (−1.35) | 30.64 | (−1.51) |
| 30% urea + 3% BLO | RT | 29.97 | 29.79 | (−0.60) | 29.63 | (−1.13) |
| | 37 C | 30.62 | 30.09 | (−1.73) | 29.97 | (−2.12) |
| | 45 C | 30.15 | 29.66 | (−1.63) | 29.45 | (−2.32) |
| 50% urea | RT | 51.77 | 51.45 | (−0.62) | 51.36 | (−0.79) |

TABLE 2-continued

| | | CONCENTRATION OF UREA (g/100 ml) | | | | |
|---|---|---|---|---|---|---|
| | | Initial (1 Day) | 45 Day | (% change) | 90 day | (% change) |
| | 37 C | 50.99 | 50.54 | (−0.88) | 50.48 | (−1.00) |
| | 45 C | 50.86 | 50.31 | (−1.08) | 50.15 | (−1.40) |
| 50% urea + | RT | 51.74 | 51.20 | (−1.04) | 50.91 | (−1.60) |
| 5% BLO | 37 C | 49.97 | 49.21 | (−1.52) | 48.97 | (−2.00) |
| | 45 C | 50.68 | 49.71 | (−1.91) | 49.45 | (−2.43) |

(RT: Room Temperature)
(Data are based on the average of 3 experiments)

EXAMPLE 3

This examples relates to the stabilization of already degraded or denaturalized urea preparations.

Figure 5:
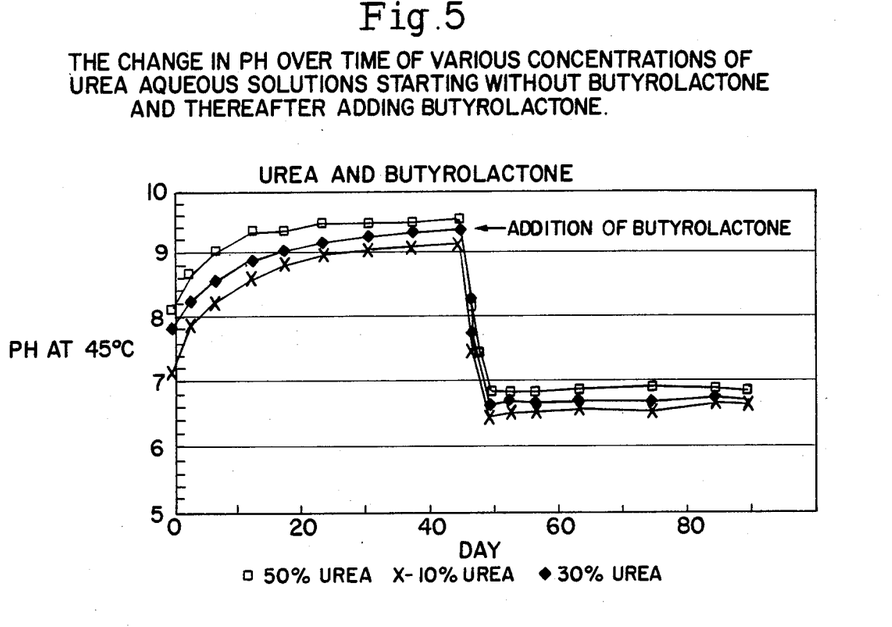
FIG. 5 is a graph showing the change in pH over time of various concentrations of urea aqueous solutions starting without butyrolactone and thereafter adding butyrolactone. Experiments were carried out at 45° C.

Samples of 50, 30, and 10 w/v percent urea aqueous solutions were made as described in EXAMPLE 1. These solutions were then sealed and maintained at a constant temperature at 45° C. for 45 days (equivalent to one year at room temperature). At day 45 the pH of these three urea solutions reached the equilibrium states of 9.50, 9.38, and 9.14 for the 50, 30, and 10 percent urea solutions respectively. All three urea solutions gave off strong ammoniacal odors. At day 45, 0.1 part by weight of gamma-butyrolactone was added per 1 part of initial weight of urea. A sudden drop of pH and disappearance of ammonia odor were observed in 1-2 days, and thereafter the pH of the each urea solution leveled off below 7.0, but above 6.0 (FIG. 5).

During the first 45 days, urea had been degraded and urea solutions lost approximately 1.1-1.4 percent of their initial concentrations. However, after the addition of gamma-butyrolactone the concentration of urea in the solutions remained essentially unchanged thereafter (TABLE 3).

TABLE 3

| CONCENTRATION OF UREA IN VARIOUS AQUEOUS SOLUTIONS (g/100 ml) | | | | |
|---|---|---|---|---|
| | Day of observation (at 45° C.) | | | |
| Urea aqueous solution | Initial | 45 (add BLO) | 60 | 90 |
| 10% (w/v) | 10.09 (pH 7.14) | 9.95 (pH 9.14) | 9.94 (pH 6.82) | 9.92 (pH 6.86) |
| 30% (w/v) | 29.97 (pH 7.85) | 29.63 (pH 9.38) | 29.60 (pH 6.82) | 29.61 (pH 6.94) |
| 50% (w/v) | 50.86 (pH 8.18) | 50.24 (pH 9.50) | 50.22 (pH 6.91) | 50.21 (pH 6.97) |

(Data are based of the average of 5 experiments)

EXAMPLES 4-7 are specific formulations for creams and lotions which may be made in accordance with the present invention. All ingredients other than the urea and BLO are well known in the art and therefore will not be discussed.

EXAMPLE 4

Concentrations of 10% urea in topical creams have been used in simple dry skin treatment. However, physio-chemical stability of the preparations change as time goes by, especially when they are kept under higher temperature.

A skin moisturizing cream in accordance with the invention having the following composition was prepared:

| | Grams |
|---|---|
| Urea USP | 10.00 |
| Butyrolactone | 1.00 |
| Glycery Stearate | 7.00 |
| Mineral Oil USP | 7.00 |
| Caprylic/Capric triglyceride | 5.00 |
| Cetearyl Alcohol/Ceteareth 20 | 4.00 |
| Glycerin 96% USP | 3.50 |
| Propylene Glycol | 3.50 |
| Dimethicone | 1.00 |
| Cetyl Alcohol | 0.50 |
| Polymer JR-400 | 0.20 |
| Preservative | 0.20 |
| EDTA tetrasodium Tetrahydrate | 0.03 |
| Butylated Hydroxytoluene | 0.03 |
| Purified Water USP | Remainder |
| | 100.00 ml |

Figure 6:
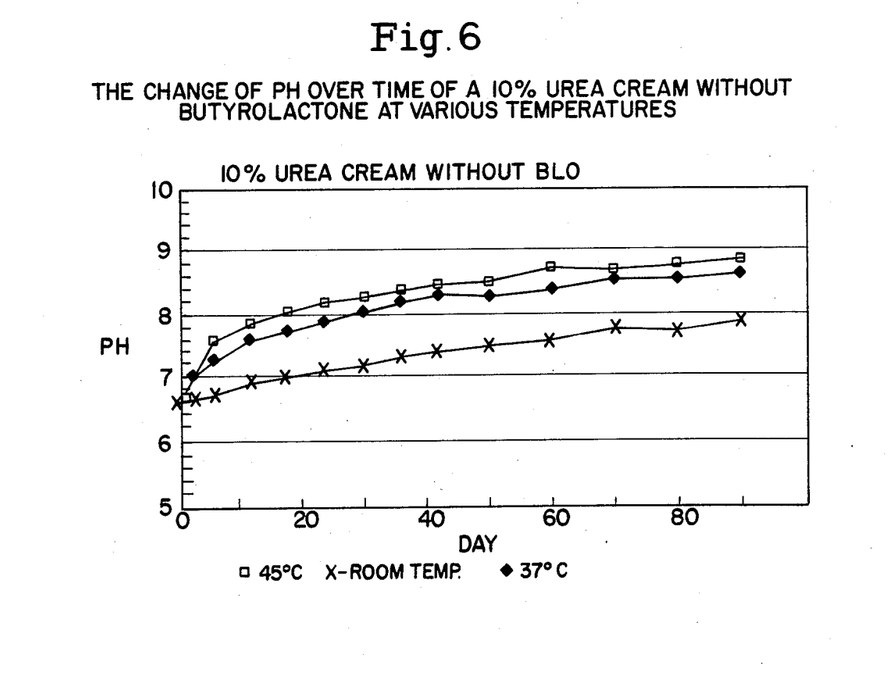
FIG. 6 is a graph showing the change in pH over time of a 10 percent urea cream without butyrolactone at various temperatures.
Figure 7:
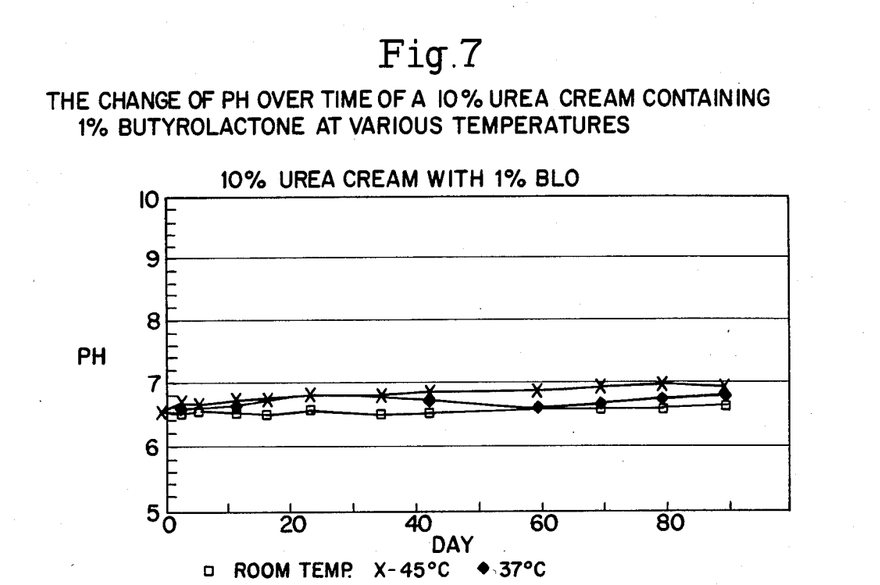
FIG. 7 is a graph showing the change in pH over time of a 10 percent urea cream containing 1 percent of butyrolactone at various temperatures.
Figure 8:
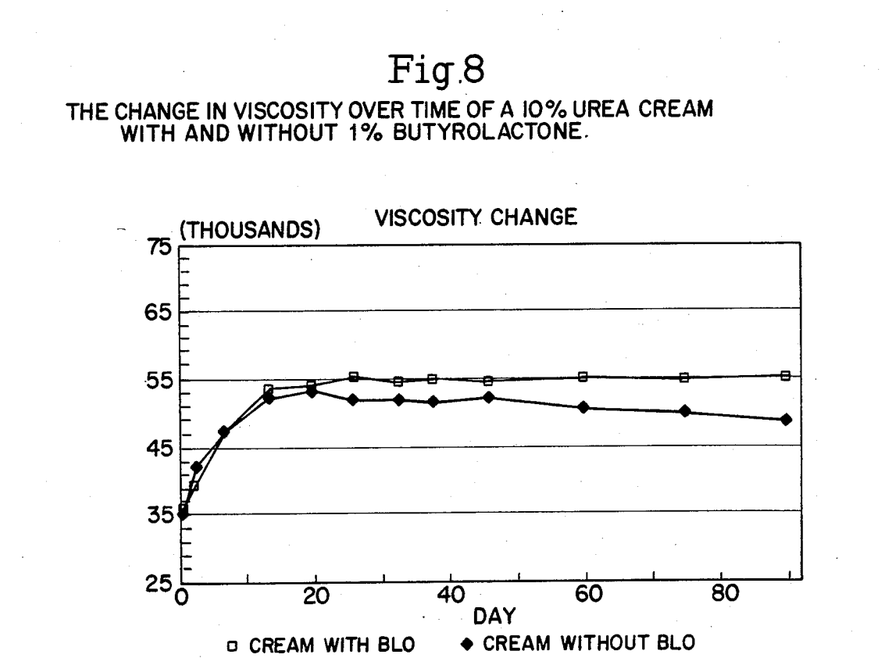
FIG. 8 is a graph showing the change in viscosity over time of a 10 percent urea cream with and without 1 percent butyrolactone. Experiments were carried out at room temperature, and viscosity was measured using a Brookfield viscometer, model LVT, with spindle No. 4.

The pH, viscosity and active urea concentrations of skin moisturizing creams made in accordance with the above composition, with and without BLO, were measured periodically over 90 days, with the initial measurements at 1 day. The results for the pH measurements are shown in FIG. 6 (without BLO) and FIG. 7 (with BLO), with tests conducted at room temperature, 37° C., and 45° C. At all three temperatures, creams without BLO showed significant pH increases, while those with BLO retained pH's of less than 7.0.

The viscosities of the room temperature test samples were also measured at regular intervals. Measurements were made with a Brookfield viscometer, model LVT, with a No. 4 spindle. Over the 90 day period, the cream with BLO maintained a constant viscosity of about 55000 centipoises, while the cream without BLO deteriorated to a viscosity of about 48000 centipoises. The results for the urea concentration measurements are given in TABLE 4. As noted, the creams without BLO destabilized so badly that 45 and 90 day measurements could not even be made.

TABLE 4

| UREA CONCENTRATION IN SKIN MOISTURIZING CREAM (g/100 ml) | | | | | | |
|---|---|---|---|---|---|---|
| Storage Condition | with/without butyrolactone | Initial | 45 Day | (% Change) | 90 Day | (% Change) |
| 45° C. | With BLO | 10.11 | 9.93 | (−1.78) | 9.89 | (−2.18) |
| | Without BLO | 10.02 | *na | | *na | |
| 37° C. | With BLO | 10.02 | 9.89 | (−1.30) | 9.86 | (−1.60) |
| | Without BLO | 10.28 | *na | | *na | |
| Room Temp. | With BLO | 10.21 | 10.19 | (−0.20) | 10.14 | (−0.69) |

TABLE 4-continued

UREA CONCENTRATION IN SKIN MOISTURIZING CREAM (g/100 ml)

| Storage Condition | with/without butyrolactone | Initial | 45 Day | (% Change) | 90 Day | (% Change) |
|---|---|---|---|---|---|---|
| | Without BLO | 10.08 | 10.02 | (−0.60) | 10.01 | (−0.69) | na: Not available
*The emulsion system of the cream became unstable at high pH. As a result, the separation of water phase and oil phase were noted.
(Data are based on the average of 3 experiments)

EXAMPLE 5

A topical lotion which contains 25 percent urea (w/v) has mild keratolytic activity and increases water uptake in the corneum, giving it a high water-binding capacity. Therefore, such lotion is rich with softeners and moisturizers to make dry, rough, thickened skin such as elbows and knees soft and supple. The following skin moisturizing lotion was prepared in accordance with the invention, having 0.08 part by weight of gamma-butyrolactone per 1 part by weight of urea.

| | Grams |
|---|---|
| Urea USP | 25.00 |
| Butyrolactone | 2.00 |
| Mineral Oil USP | 6.00 |
| Propylene Glycol USP | 4.00 |
| Glycerin 96% USP | 4.00 |
| PEG-50 Stearate | 2.50 |
| Hydrogenated Lanolin | 2.00 |
| Sorbitan Monostearate NF | 1.50 |
| Magnesium Aluminum Silicate | 1.00 |
| Propylene Glycol Monostearate NF | 1.00 |
| Glyceryl Monostearate | 1.00 |
| Cetyl Alcohol NF | 0.50 |
| Fragrance | 0.20 |
| Preservative | 0.10 |
| EDTA Tetrasodium Tetrahydrate | 0.07 |
| Purified Water USP | Remainder |
| | 100.00 ml |

Figure 9:
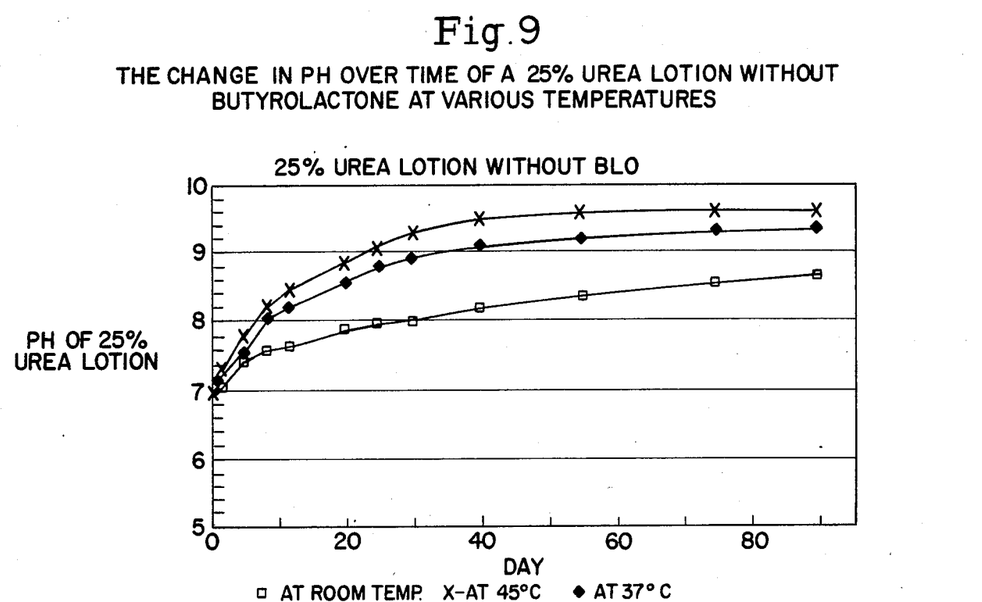
FIG. 9 is a graph showing the change in pH over time of a 25 percent urea lotion without butyrolactone at various temperatures.
Figure 10:
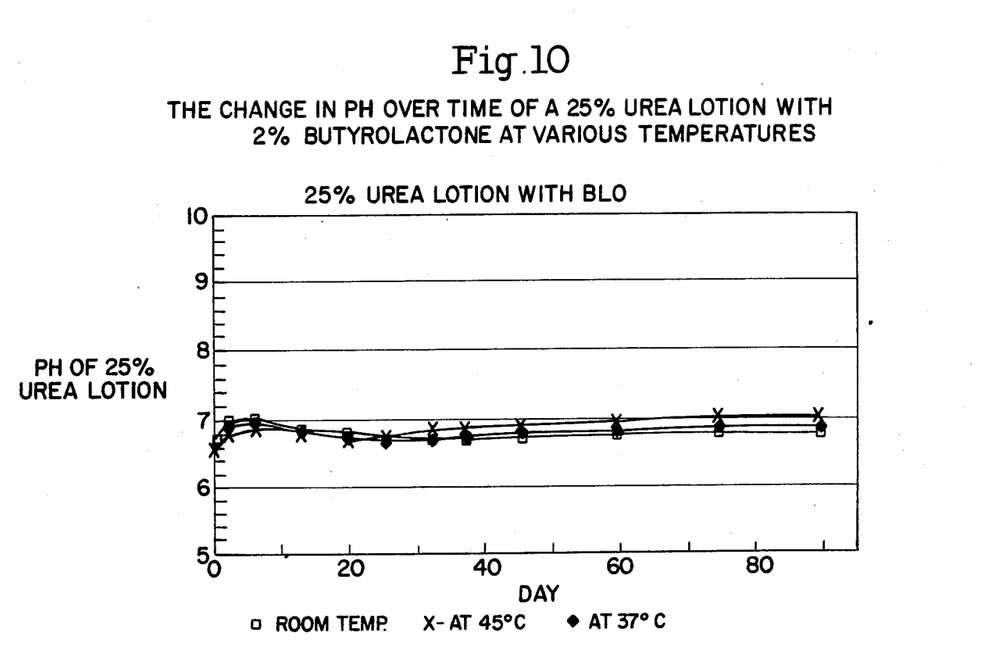
FIG. 10 is a graph showing the change in pH over time of a 25 percent urea lotion containing 2 percent butyrolactone at various temperatures.
Figure 11:
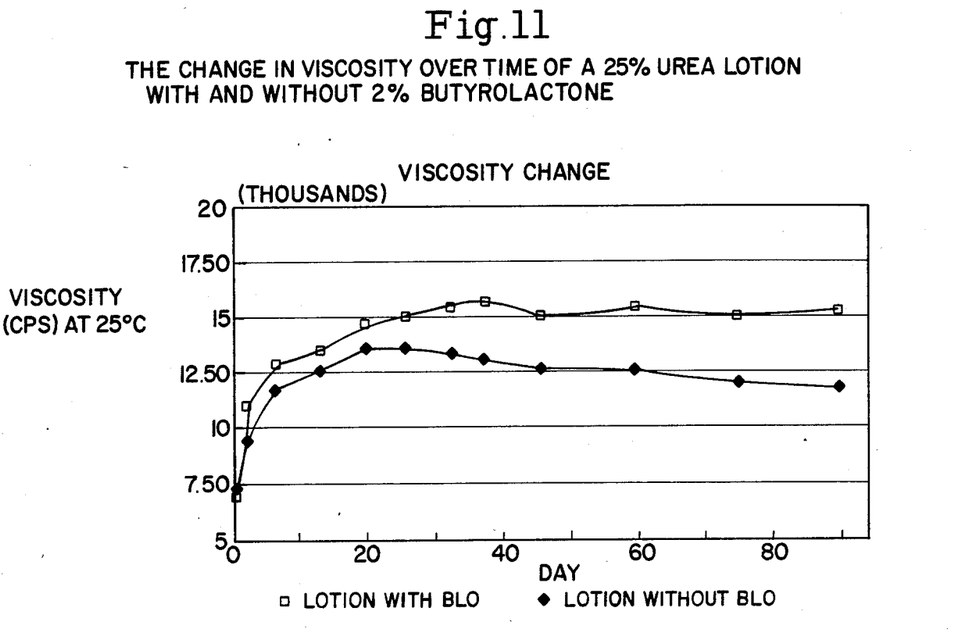
FIG. 11 is a graph showing the change in viscosity over time of a 25 percent urea lotion with and without 2 percent butyrolactone. Experiments were carried out at room temperature, and viscosity was measured using a Brookfield viscometer, model LVT, with spindle No. 4.

The pH, viscosity and urea concentrations of the above preparations were measured as in EXAMPLE 4. The results are shown in FIGS. 9, 10 and 11, and TABLE 5.

TABLE 5

UREA CONCENTRATION IN SKIN MOISTURIZING LOTION

| | Initial | 45 Days | (% Change) | 90 Days | (% Change) |
|---|---|---|---|---|---|
| Room Temp. | | | | | |
| with BLO | 25.31 | 25.29 | (−0.08) | 25.24 | (−0.27) |
| without BLO | 25.17 | 25.06 | (−0.44) | 24.96 | (−0.83) |
| 37° C. BLO | | | | | |
| with BLO | 25.29 | 25.15 | (−0.55) | 25.08 | (−0.83) |
| without BLO | 25.02 | *na | *na | | |
| 45° C. BLO | | | | | |
| with BLO | 24.99 | 24.86 | (−0.52) | 24.77 | (−0.88) |
| without BLO | 25.24 | *na | *na | | | no: not available
*The emulsion system of this lotion became unstable as pH rose to 9.0. As a result, the separation of water phase and oil phase was observed.
(Data are based on the average of 6 experiments)

EXAMPLES 6 AND 7

Topical corticosteroid creams with 10 percent urea were tested. Corticosteroids are eminently effective in treating atopic dermatitis. Recent reports have indicated that the improvement induced by topical corticosteroids was enhanced by the addition of urea to the formulation. (R. J. Feldmann and H. I. Mailback, *Arch Dermatol,* 109. 58 (1974), P. J. W. Ayres and G. Hooper, *Brit. J. Dermatol,* 99; 307 (1978), and R. Woodford and B. W. Barry, *Current Therap.* Res. 35. 759 (1984).

Two corticosteroids, triamcinolone acetonide and bethamethasone valerate were incorporated into preparations in accordance with the present invention. EXAMPLE 6, a skin lotion containing triamcinolone acetonide, had the following composition:

| | Grams |
|---|---|
| Triamcinilone Acetonide | 0.10 |
| Urea USP | 10.00 |
| Butyrolactone | 1.00 |
| Caprylic/Capric Triglyceride | 5.00 |
| Mineral Oil USP | 5.00 |
| Cetearyl Alcohol/Ceteareth-20 | 4.00 |
| Propylene Glycol USP | 3.00 |
| Mineral Oil/Lanolin Alcohol | 3.00 |
| Lanolin Alcohol Acetate | 2.00 |
| Glyceryl Stearate | 2.00 |
| Glycerin 96% USP | 2.00 |
| Dimethicone | 1.00 |
| Cetyl Alcohol NF | 0.50 |
| Soy Phosphatide | 0.50 |
| Carbomer 934 | 0.10 |
| EDTA Tetrasodium Tetrahydrate | 0.05 |
| Butylated Hydroxytoluene | 0.03 |
| Preservative | 0.30 |
| Purified Water USP | Remainder |
| | 100.00 ml |

Figure 12:
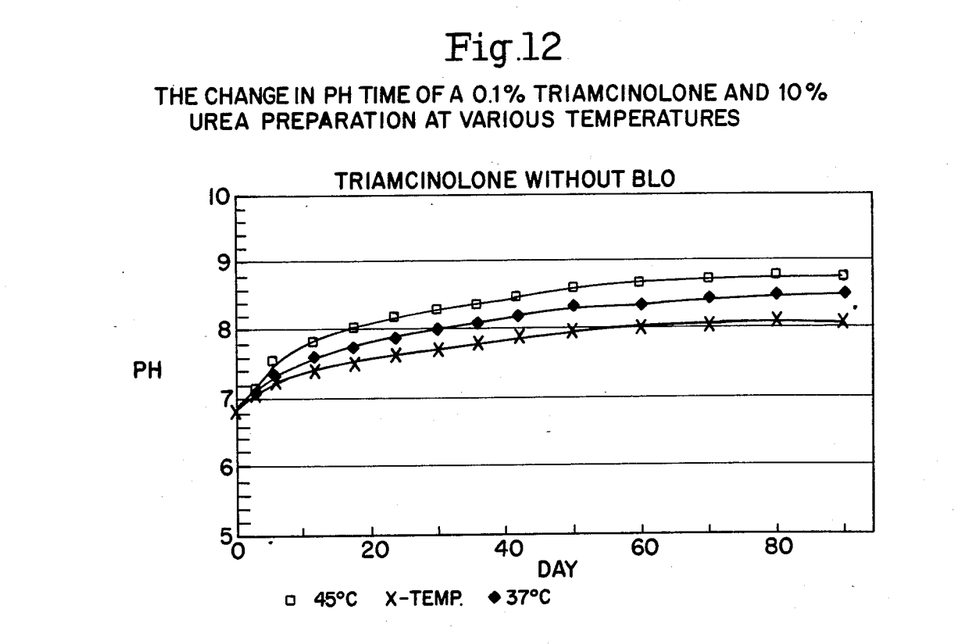
FIG. 12 is a graph showing the change in pH over time of a 0.1 percent triamcinolone and 10 percent urea preparation at various temperatures.
Figure 13:
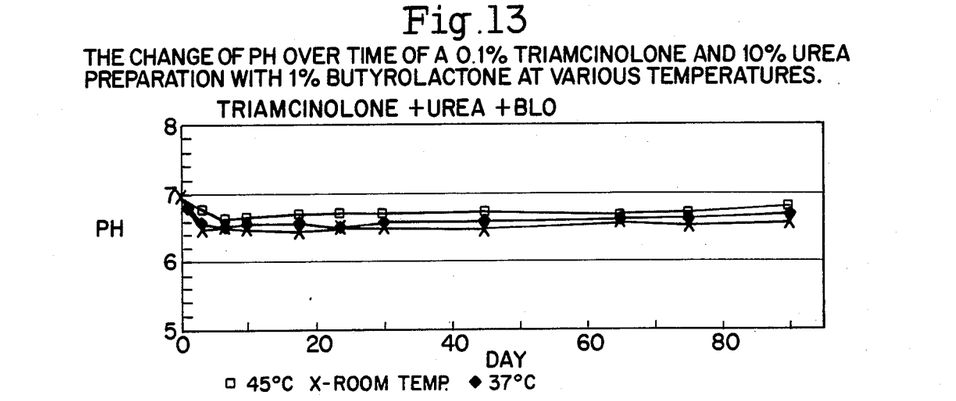
FIG. 13 is a graph showing the change in pH over time of a 0.1 percent triamcinolone and 10 percent urea preparation with 1 percent butyrolactone at various temperatures.

The data in TABLE 6 and as shown in FIGS. 12 and 13 were obtained from compositions with butyrolactone and without butyrolactone in this triamcinolone lotion. As the data in TABLE 6 indicates, urea with and without butyrolactone, did not significantly affect the amount of available triamcinolone acetonide in these lotions.

TABLE 6

TRIAMCINILONE ACETONIDE CONCENTRATION (g/100 ml) AT 45° C.

| | Initial | 45 Days | 90 Days |
|---|---|---|---|
| WITH BLO | 0.105 | 0.103 | 0.103 |
| WITHOUT BLO | 0.108 | 0.102 | 0.098 |

(Data are based on the average of 3 experiments)

EXAMPLE 7, a skin cream containing betamethasone valerate, had the following composition:

| | |
|---|---|
| Betamethasone Valerate | 0.10 |
| Urea USP | 10.00 |
| Butyrolactone | 1.00 |
| Mineral Oil USP | 7.00 |
| Propylene Glycol USP | 4.00 |
| Glycerin 96% USP | 3.00 |
| Lanolin Alcohol Acetate | 3.00 |
| Glyceryl Stearate | 2.00 |
| PEG-50 Stearate | 1.00 |
| Glycol Stearate | 1.00 |
| Caprylic/Capric Triglyceride | 1.00 |
| Squalane | 1.00 |

-continued

| | |
|---|---|
| Dimethicone | 1.00 |
| Myristyl Myristate | 1.00 |
| Hydrogenated Lanolin | 1.00 |
| Stearic Acid NF | 1.00 |
| Cetyl Alcohol NF | 1.00 |
| Triethanolamine | 0.35 |
| Soy Phosphatide | 0.30 |
| Carbomer 934 | 0.20 |
| Magnesium Aluminum Silicate | 0.20 |
| Butylated Hydroxytoluene | 0.03 |
| Preservative | 0.30 |
| Purified Water USP | Remainder |
| | 100.00 ml |

Figure 14:
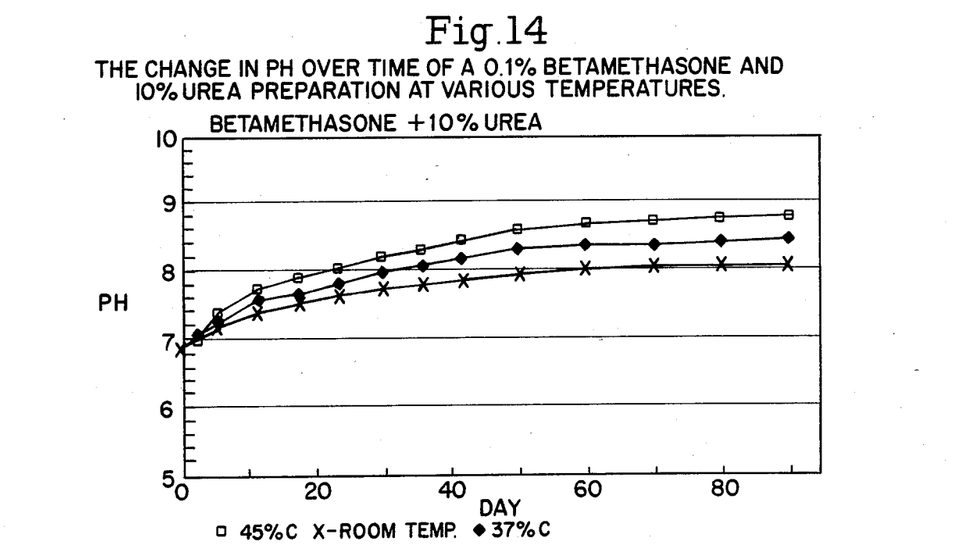
FIG. 14 is a graph showing the change of pH over time of a 0.1 percent betamethasone and 10 percent urea preparation at various temperatures.
Figure 15:
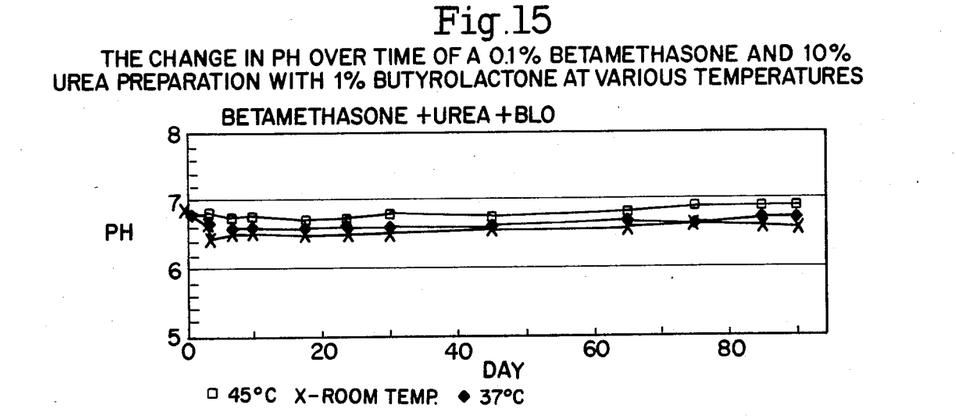
FIG. 15 is a graph showing the change of pH over time of a 0.1 percent betamethasone and 10 percent urea preparation with 1 percent butyrolactone at various temperatures. (Data on above from FIG. 1 to FIG. 15 are the average of at least three determinations)

The data in TABLE 7 and as shown in FIGS. 14 and 15 were obtained with butyrolactone and without butyrolactone in 0.1 percent betamethasone creams with the above composition. As the data in TABLE 7 indicates, urea with or without butyrolactone did not significantly affect the amount of betamethasone valerate available.

TABLE 7

| BETAMETHASONE VALERATE CONCENTRATION (g/100 ml) AT 45° C. | | | |
|---|---|---|---|
| | Initial | 45 days | 90 days |
| WITH BLO | 0.109 | 0.106 | 0.107 |
| WITHOUT BLO | 0.105 | 0.102 | 0.100 |

(Data are based on the average of 3 experiments)

This invention has been disclosed and described herein in what is believed to be its preferred embodiments. However, it should be noted that variations may occur to those skilled in the art on reading this disclosure, and such are considered to be within the scope of this invention.

What is claimed is:

1. A pharmaceutical preparation comprising about 1 to about 50 percent by weight urea and about 0.05 to about 30 percent by weight of a lactone selected from the group consisting of:

| | |
|---|---|
| gamma-butyrolactone, | beta-butyrolactone, |
| gamma-thiobutyrolactone, | 2-acetyl-gamma-butyrolactone, |
| gamma-valerolactone, | delta-valerolactone, |
| gamma-octanoiclactone, and | epsilon-caprolactone. |

2. The pharmaceutical preparation of claim 1, wherein the lactone is gamma-butyrolactone.

3. The pharmaceutical preparation of claim 1, wherein the lactone is present in an amount ranging from about 0.05 to about 10 percent by weight.

4. The pharmaceutical preparation of claim 3 wherein the pH is maintained in the range of from about 6.0 to about 7.0.

5. The pharmaceutical preparation of claim 3 wherein the lactone is present in an amount ranging from about 0.05 to about 2.5 percent by weight.

6. The pharmaceutical preparation of claim 1, wherein the lactone is present in an amount ranging from about 0.05 to 0.1 parts by weight per 1 part by weight of urea.

7. A method for stabilizing the urea in a pharmaceutical preparation containing about 1 to about 50 percent by weight urea comprising adding about 0.05 to about 30 percent by weight of a lactone to said pharmaceutical preparation, said lactone being selected from group consisting of:

| | |
|---|---|
| gamma-butyrolactone, | beta-butyrolactone, |
| gamma-thiobutyrolactone, | 2-acetyl-gamma-butyrolactone, |
| gamma-valerolactone, | delta-valerolactone, |
| gamma-octanoiclactone, and | epsilon-caprolactone. |

8. The method of claim 7 wherein the lactone is gamma-butyrolactone.

9. The method of claim 7 wherein the lactone is added in an amount ranging from about 0.05 to about 10 percent by weight.

10. The method of claim 9 wherein the pH is maintained in the range of from about 6.0 to about 7.0.

11. The method of claim 7 wherein the lactone is added in an amount ranging from about 0.05 to about 2.5 percent by weight.

12. The method of claim 7 wherein the lactone is added in an amount ranging from about 0.05 to about 0.1 parts by weight per 1 part by weight of the urea.

13. A method for stabilizing and reducing the pH to below about 7.0 of degraded pharmaceutical preparations containing about 1 to about 50 percent by weight urea comprising adding about 0.05 to about 30 percent by weight of a lactone to said partially degraded pharmaceutical preparation, said lactone being selected from the group consisting of:

| | |
|---|---|
| gamma-butyrolactone, | beta-butyrolactone, |
| gamma-thiobutyrolactone, | 2-acetyl-gamma-butyrolactone, |
| gamma-valerolactone, | delta-valerolactone, |
| gamma-octanoiclactone, and | epsilon-caprolactone. |

14. The method of claim 13 wherein said lactone is gamma-butyrolactone.

* * * * *